US008124622B2

(12) United States Patent
Yokoyama et al.

(10) Patent No.: US 8,124,622 B2
(45) Date of Patent: Feb. 28, 2012

(54) TRIGLYCERIDE-LOWERING AGENT AND HYPERINSULINISM-AMELIORATING AGENT

(75) Inventors: Toru Yokoyama, Higashimurayama (JP); Taro Aoki, Higashimurayama (JP)

(73) Assignees: Kowa Co., Ltd., Nagoya-shi (JP); Nissan Chemical Industries, Ltd., Tokyo (JP)

( * ) Notice: Subject to any disclaimer, the term of this patent is extended or adjusted under 35 U.S.C. 154(b) by 653 days.

(21) Appl. No.: 12/293,433

(22) PCT Filed: Mar. 28, 2007

(86) PCT No.: PCT/JP2007/000316
§ 371 (c)(1),
(2), (4) Date: Sep. 18, 2008

(87) PCT Pub. No.: WO2007/111027
PCT Pub. Date: Oct. 4, 2007

(65) Prior Publication Data
US 2009/0291980 A1 Nov. 26, 2009

(30) Foreign Application Priority Data

Mar. 29, 2006 (JP) .................. 2006-090160
Jul. 27, 2006 (JP) .................. 2006-204608

(51) Int. Cl.
*A61K 31/47* (2006.01)
*A61K 31/44* (2006.01)
(52) U.S. Cl. .................. 514/311; 514/314; 514/356
(58) Field of Classification Search .................. 514/311, 514/314, 356
See application file for complete search history.

(56) References Cited

U.S. PATENT DOCUMENTS

| 5,011,930 | A | 4/1991 | Fujikawa et al. |
| 6,455,574 | B1 | 9/2002 | Buch |
| 7,019,010 | B2 | 3/2006 | Cohen |
| 2002/0025981 | A1 | 2/2002 | Buch et al. |
| 2002/0028826 | A1 | 3/2002 | Robl et al. |
| 2002/0099046 | A1 | 7/2002 | Scott |
| 2003/0114497 | A1 | 6/2003 | Alani et al. |
| 2003/0181500 | A1 | 9/2003 | Lee et al. |
| 2004/0253305 | A1 | 12/2004 | Luner et al. |

FOREIGN PATENT DOCUMENTS

| JP | 1 279866 | 11/1989 |
| JP | 2001 514224 | 9/2001 |
| JP | 2002 145770 | 5/2002 |
| JP | 2004 503541 | 2/2004 |
| JP | 2004 210797 | 7/2004 |
| JP | 2005 501051 | 1/2005 |
| JP | 2005 41875 | 2/2005 |
| JP | 2005 504113 | 2/2005 |
| JP | 2005 89300 | 4/2005 |
| WO | 2004 110406 | 12/2004 |
| WO | WO 2005/097191 A2 | 10/2005 |
| WO | WO 2005/097191 A3 | 10/2005 |

OTHER PUBLICATIONS

Aoki et al., "Triglyceride-lowering effect of pitvastatin in a rat model of postprandial lipemia", European Journal of Pharmacology, vol. 444, No. 1-2, pp. 107-113 (2002).*
Sone et al., "HMG-CoA reductase inhibitor decreases small dense low-density lipoprotein and remnant-like particle cholesterol in patients with type-2 diabetes", Life Sciences, vol. 71, No. 20, pp. 240-2412 (2002).*
Ahaneku et al., "Influence of Baseline Values on Lipids, Lipoproteins and Fibrinolytic Parameters During Amlodipine Treatment of Hypertension in Japanese Patients", Pharmacological Research, vol. 41, No. 1, pp. 73-77 (2000).*
Ackerman et al., "Fructose-Induced Fatty Liver Disease Hepatic Effects of Blood Pressure and Plasma Triglyceride Reduction", Hypertension, vol. 45, No. 5, pp. 1012-1018 (2005).*
Charles E. Rackley, "Monotherapy with HMG-CoA Reductase Inhibitors and Secondary Prevention in Coronary Artery Disease." Clin. Cardiol, vol. 19, Sep. 19, 1996. pp. 683-689.
Therapeutic Research, vol. 24, No. 7, 2003. pp. 1383-1389.
G. Leonetti. "Effects of nilvadipine and amlodipine in patients with mild to moderate essential hypertension: a double blind, prospective, randomised clinical trial." Current Medical Research and Opinion, vol. 21, No. 6, 2005, pp. 951-958.
Roberto Fogari, et al. "Effects of different antihypertensive drugs on plasma fibrinogen in hypertensive patients." Br. J. Clin Pharmac, vol. 39, 1995, pp. 471-476.
Zvi Ackerman, et al. "Fructose-Induced Fatty Liver Disease: Hepatic Effects of Blood Pressure and Plasma Triglyceride Reduction." Hypertension: Journal of the American Heart Association. 45, May 2005, 8 Pages.
Roberto Fogari, et al. "Effect of Amlodipine-Atorvastatin Combination on Fibrinolysis in Hypertensive Hypercholesterolemic Patients With Insulin Resistance." The American Journal of Hypertension, vol. 17, No. 9, Sep. 2004, pp. 823-827.
Jean-Francois Dorval, et al. "Reaching Recommended Lipid and Blood Pressure Targets with Amlodipine/Atorvastatin Combination in Patients With Coronary Heart Disease." The American Journal of Cardiology, vol. 95, Jan. 15, 2005, pp. 249-253.
Sweder W.E. Van De Poll, et al. "Effects of amlodipine, atorvastatin and combination of both on advanced atherosclerotic plaque in APOE*3-Leiden transgenic mice." Journal of Molecular and Cellular Cardiology, vol. 35, 2003, pp. 109-118.

(Continued)

*Primary Examiner* — Kevin E Weddington
(74) *Attorney, Agent, or Firm* — Oblon, Spivak, McClelland, Maier & Neustadt, L.L.P.

(57) ABSTRACT

The present invention is directed to a triglyceride-lowering agent, exhibiting excellent triglyceride-lowering effect and a hyperinsulinemia-ameliorating agent.
The triglyceride-lowering agent and hyperinsulinemia-ameliorating agent are characterized by containing a pitavastatin compound, and amlodipine or a salt thereof.

12 Claims, 2 Drawing Sheets

OTHER PUBLICATIONS

Mitsuki Shimabukuro, et al., "The Effect of pitavastatin on the endothelial-dependent Vasolidation", Therapeutic Research, vol. 24, No. 7, 2003 pp. 1383-1389 (previously filed on Jan. 6, 2010; submitting partial English translation).

Fujino, H. et al., "Interaction between Several Medicines and Statins", Arzneimittel-Forschung, vol. 53, No. 3, pp. 145-153, (2003).

* cited by examiner

\*\* : p＜0.01

*: p<0.05

TRIGLYCERIDE-LOWERING AGENT AND HYPERINSULINISM-AMELIORATING AGENT

CROSS-REFERENCE TO RELATED APPLICATIONS

This application is a 371 of PCT/JP07/00316 filed Mar. 28, 2007 and claims the benefit of JP 2006-090160 filed Mar. 29, 2006 and JP 2006-204608 filed Jul. 27, 2006.

TECHNICAL FIELD

The present invention relates to a triglyceride-lowering agent, exhibiting excellent triglyceride-lowering effect and a hyperinsulinemia-ameliorating agent.

BACKGROUND ART

Triglyceride is the predominant component of blood neutral lipid and, physiologically, is utilized as an energy source in the peripheral tissue. Hypertriglyceridemia, involving an increased blood triglyceride level, is thought to be a risk factor of arteriosclerosis, and actually is employed as a diagnostic standard for metabolic syndrome. Therefore, for patients suffering or suspected of suffering hypertriglyceridemia, blood triglyceride is desirably lowered to an appropriate level by use of a drug or through other methods.

Hyperinsulinemia is a disease caused by over-secretion of insulin from the islets of Langerhans of the pancreas, which over-secretion compensates hyperglycemia occurring in diabetes or a pre-diabetes stage. When insulin has been over-secreted, pancreatic hormone secretion ability and sugar-utilization in the peripheral tissue are impaired, and blood insulin is maintained at high level, thereby causing a variety of complications. For example, retinopathy, aggravation of nephropathy, and induction of differentiation of fat cells and other cells occur. Therefore, amelioration of hyperinsulinemia is effective for the prevention of such complications and obesity, particularly prevention of accumulation of visceral fat. Thus, there is the demand for a high-efficacy hyperinsulinemia-ameliorating agent.

The aforementioned pathological conditions and diseases are closely related to metabolic syndrome, whose diagnosis standards have recently been published, and are classified as life-style-related diseases including hyperlipidemia. According to the diagnosis standard, metabolic syndrome is defined as a condition in which visceral-fat-increased obesity is complicated with two or more of hyperglycemia, hypertension, and hyperlipidemia.

Statins (HMG-CoA reductase inhibitors) are administered to hyperlipidemia patients, since intense cholesterol-lowering action thereof is expected.

Statins are known to have an action on neutral lipid; specifically, a slight triglyceride-lowering action concomitant with a cholesterol-lowering action (see, for example, Non-Patent Document 1). However, when statin is used singly, triglyceride-lowering action thereof is insufficient. Thus, there has been proposed use of statin in combination with a triglyceride-lowering agent; for example, a fibrate-type drug. However, rhabdomyolysis has been reported to occur as an adverse side effect mainly in kidney disorder patients, when such a fibrate-type drug having strong triglyceride-lowering action and statin are used in combination. Thus, this combined administration must be carried out very carefully.

Statins are also known to have an action on insulin; specifically, a slight insulin-resistance-ameliorating action concomitant with a cholesterol-lowering action (see, for example, Non-Patent Document 2). However, no effect of statins has been known to ameliorate hyperinsulinemia. When statin is used singly, the insulin-resistance ameliorating action thereof is insufficient. Thus, there have been proposed the use of statin in combination with other insulin-resistance-ameliorating agents such as metformin or glitazones and use thereof in combination with a hypoglycemic agent such as a sulfonylurea agent. However, when statin is used with another agent such as an insulin-resistance-ameliorating agent or a hypoglycemic agent, control of blood sugar level is difficult, possibly causing a fatal hypoglycemia condition. Thus, this combined administration must also be carried out very carefully.

Generally, in many patients suffering hyperlipidemia, diabetes, metabolic syndrome, etc., hypertriglyceridemia occurs due to obesity or impairment in a metabolic function. Also, hyperinsulinemia occurs in many cases due to insulin secretion hyperfunction of the pancreas, which hyperfunction compensates for hyperglycemia. Therefore, there has been the demand for a drug which reduces adverse side effects and which promotes effective triglyceride-lowering action, as well as the demand for a drug which promotes hyperinsulinemia-ameliorating action, which drugs are used in combination with stain serving as a hyperlipidemia-treating agent.

Meanwhile, calcium antagonist is employed as a therapeutic agent for hypertension and angina pectoris, but neither triglyceride-lowering action nor hyperinsulinemia-ameliorating action is envisaged in use thereof, in view of the action mechanism of the antagonist. Furthermore, amlodipine besylate—a type of calcium antagonist—has been reported to increase the triglyceride level of hypertension patients (see Non-Patent Document 3). Also, amlodipine has been reported to give no significant effect on the plasma triglyceride level of hypertension patients (see Non-Patent Document 4). In animal models, when administered to fructose-loaded hypertriglyceridemia rats, amlodipine besylate has no significant triglyceride-lowering action or hyperinsulinemia-ameliorating action (see Non-Patent Document 5).

Notably, the main action of calcium antagonist is a hypotensive activity on the basis of selectively binding to cell membrane potential-dependent calcium channel, reducing flow of calcium ions into cells, and relaxing smooth muscle of coronary and peripheral vessels. Hitherto, direct lipid-decomposing action has not been reported, nor has insulin biosynthesis, secretion, and decomposing action.

Statin has a cholesterol-lowering action, whereas a calcium antagonist has a hypotensive action. Therefore, in the clinical field, the two agents are administered in combination to patients suffering from both hyperlipidemia and hypertension. Some scientific documents report administration of atorvastatin and amlodipine in combination to patients suffering from a coronary arterial disease. In the studies, there has been found no difference between a plasma triglyceride level of the combined administration group and that of an atorvastatin single administration group (see Non-Patent Documents 6 and 7). In addition, these documents do not disclose plasma insulin level. Similarly, in animal models (genetically modified mice), no difference has been found between the plasma triglyceride level of an atorvastatin single administration group and that of an atorvastatin-amlodipine combined administration group (see Non-Patent Document 8). The document does not describe that the combined administration gives an effect on the plasma insulin level. Some patent publications (Laid-Open) disclose combined administration of statin and amlodipine (see Patent Documents 1 to 3). However, these patent documents are silent regarding the effects of combined administration of statin and a calcium antagonist on the triglyceride-lowering action and on hyperinsulinemia.

Patent Document 1:
International Publication WO99/11259, pamphlet
Patent Document 2:
International Publication WO99/11260, pamphlet
Patent Document 3:
International Publication WO99/11263, pamphlet
Non-Patent Document 1:
Clin. Cardiol., 19(9): 683-9, 1996
Non-Patent Document 2:
Therapeutic Research, 24: 1383-1389, 2003
Non-Patent Document 3:
Curr. Med. Res. Opin., 21(6): 951-8, 2005
Non-Patent Document 4:
Br. J. Clin. Pharmacol., 39(5): 471-6, 1995
Non-Patent Document 5:
Hypertension, 45: 1012-18, 2005
Non-Patent Document 6:
Am. J. Hypertension, 17: 823-827, 2004
Non-Patent Document 7:
Am. J. Cardiol., 95: 249-253, 2005
Non-Patent Document 8:
J. Mol. Cell. Cardiol., 35: 109-118, 2003

DISCLOSURE OF THE INVENTION

Problems to be Solved by the Invention

An object of the present invention is to provide a drug having excellent triglyceride-lowering action and hyperinsulinemia-ameliorating action and providing reduced adverse side effects.

Means for Solving the Problems

In view of the foregoing, the present inventors have conducted extensive studies and, surprisingly, have found that remarkable triglyceride-lowering action and hyperinsulinemia-ameliorating action can be obtained through employment in combination of a pitavastatin compound such as pitavastatin calcium and amlodipine—known as a calcium antagonist—or a salt thereof. The present invention has been accomplished on the basis of this finding.

Accordingly, the present invention provides a triglyceride-lowering agent, characterized by containing a pitavastatin compound, and amlodipine or a salt thereof.

The present invention also provides a preventive and/or therapeutic agent for hypertriglyceridemia, characterized by containing a pitavastatin compound, and amlodipine or a salt thereof.

The present invention also provides a hyperinsulinemia-ameliorating agent, characterized by containing a pitavastatin compound, and amlodipine or a salt thereof.

The present invention also provides a preventive and/or therapeutic agent for hyperinsulinemia, characterized by containing a pitavastatin compound, and amlodipine or a salt thereof.

The present invention also provides a metabolic-syndrome-ameliorating agent, characterized by containing a pitavastatin compound, and amlodipine or a salt thereof.

The present invention also provides a preventive and/or therapeutic agent for metabolic syndrome, characterized by containing a pitavastatin compound, and amlodipine or a salt thereof.

The present invention also provides a method for lowering triglyceride, characterized by comprising administering a pitavastatin compound, and amlodipine or a salt thereof to a subject in need thereof.

The present invention also provides a method for prevention and/or treatment of hypertriglyceridemia, characterized by comprising administering a pitavastatin compound, and amlodipine or a salt thereof to a subject in need thereof.

The present invention also provides a method for ameliorating hyperinsulinemia, characterized by comprising administering a pitavastatin compound, and amlodipine or a salt thereof to a subject in need thereof.

The present invention also provides a method for prevention and/or treatment of hyperinsulinemia, characterized by comprising administering a pitavastatin compound, and amlodipine or a salt thereof to a subject in need thereof.

The present invention also provides a method for ameliorating metabolic syndrome, characterized by comprising administering a pitavastatin compound, and amlodipine or a salt thereof to a subject in need thereof.

The present invention also provides a method for prevention and/or treatment of metabolic syndrome, characterized by comprising administering a pitavastatin compound, and amlodipine or a salt thereof to a subject in need thereof.

The present invention also provides use of a pitavastatin compound, and amlodipine or a salt thereof for producing a triglyceride-lowering agent.

The present invention also provides use of a pitavastatin compound, and amlodipine or a salt thereof for producing a preventive and/or therapeutic agent for hypertriglyceridemia.

The present invention also provides use of a pitavastatin compound, and amlodipine or a salt thereof for producing a hyperinsulinemia-ameliorating agent.

The present invention also provides use of a pitavastatin compound, and amlodipine or a salt thereof for producing a preventive and/or therapeutic agent for hyperinsulinemia.

The present invention also provides use of a pitavastatin compound, and amlodipine or a salt thereof for producing a metabolic-syndrome-ameliorating agent.

The present invention also provides use of a pitavastatin compound, and amlodipine or a salt thereof for producing a preventive and/or therapeutic agent for metabolic syndrome.

Effects of the Invention

According to the present invention, there can be provided a triglyceride-lowering agent and a preventive and/or therapeutic agent for hypertriglyceridemia, exhibiting excellent triglyceride-lowering effect and less adverse side effects. According to the present invention, there can be provided a hyperinsulinemia-ameliorating agent and a preventive and/or therapeutic agent for hyperinsulinemia, exhibiting excellent hyperinsulinemia-ameliorating effect and less adverse side effects. According to the present invention, hypertriglyceridemia and hyperinsulinemia of a hyperlipidemia patient can be effectively prevented and/or treated through administration of a pitavastatin compound, and amlodipine or a salt thereof in combination. According to the present invention, prevention and treatment of metabolic syndrome and ameliorating the condition of metabolic syndrome can be realized.

BEST MODES FOR CARRYING OUT THE INVENTION

Figure 1:
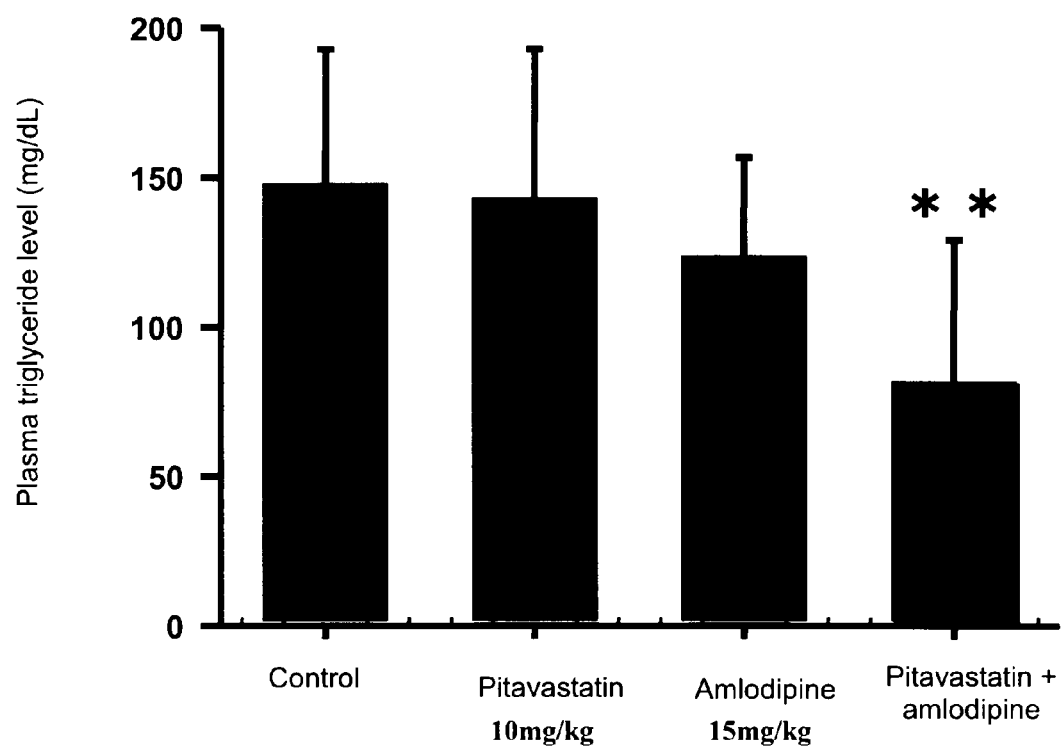
FIG. 1: A graph showing an effect of single or combined administration of pitavastatin calcium (described simply as pitavastatin) and amlodipine besylate (described simply as amlodipine) on plasma triglyceride level.

The pitavastatin compound employed in the present invention encompasses pitavastatin, a salt thereof, a lactone form thereof, a hydrate of any of these, and a solvate of any of these with the solvent which is pharmaceutically acceptable. The pitavastatin compound has a cholesterol synthesis inhibitory activity based on inhibition of HMG-CoA reductase and is known to serve as a hyperlipidemia therapeutic agent. Examples of the salt of pitavastatin include alkali metal salts such as a sodium salt and a potassium salt; alkaline earth metal salts such as a calcium salt and a magnesium salt; organic amine salts such as a phenethylamine salt; and an ammonium salt. Of these, salts of pitavastatin is preferred, with the calcium salt and the sodium salt being particularly preferred.

The pitavastatin compound may be produced through a method disclosed in U.S. Pat. No. 5,856,336 or in Japanese patent Application Laid-Open (kokai) No. 1-279866.

As mentioned above, the amlodipine or a salt thereof employed in the present invention is a calcium antagonist. Among these species, amlodipine besylate is readily available as a commercial product. No particular limitation is imposed on the salt of amlodipine, so long as the salt is pharmaceutically acceptable. Examples of the salt include inorganic acid salts such as hydrochloride, sulfate, nitrate, hydrobromide, and phosphate; and organic acid salts such as acetate, trifluoroacetate, fumarate, maleate, lactate, tartrate, citrate, succinate, malonate, methanesulfonate, p-toluenesulfonate, besylate (benzenesulfonate), camsylate (camphorsulfonate), ethanesulfonate, and nicotinate. Of these, besylate and camsylate are preferred, with besylate being particularly preferred.

According to the present invention, a pitavastatin compound, and amlodipine or a salt thereof are administered in combination. As shown in the Example hereinbelow, when a pitavastatin compound, and amlodipine or a salt thereof are administered in combination to fructose-loaded hypertriglyceridemia rats (evaluation group), the plasma triglyceride level and the plasma insulin level are considerably lowered, and hypertriglyceridemia and hyperinsulinemia are ameliorated, as compared with the case where each of the two agent is singly administered. Therefore, the drug of the present invention is useful for the prevention and/or treatment of hypertriglyceridemia and hyperinsulinemia.

The pitavastatin compound and amlodipine or a salt thereof contained in the drug of the present invention may be administered through a route appropriately selected in accordance with conditions of a patient in need thereof. Any of the dosage forms including powder, granules, dry syrup, tablets, capsules, and injections may be employed. The dosage forms may be produced by blending a pitavastatin compound, and amlodipine or a salt thereof with a pharmaceutically acceptable carrier, and processing through a routine method known to people in the art.

In one preparation procedure of an oral solid formulation, a vehicle and an optional additive such as a binder, a disintegrant, a lubricant, a colorant, a sweetening agent, or a flavoring agent, are added to the agents, and the mixture is processed, through a routine method, into tables, granules, powder, capsules, etc. Such additives may be those generally employed in the art. Examples of the vehicle include lactose, sodium chloride, glucose, starch, microcrystalline cellulose, and silicic acid. Examples of the binder include water, ethanol, propanol, simple syrup, gelatin liquid, hydroxypropyl cellulose, methyl cellulose, ethyl cellulose, shellac, calcium phosphate, and poly(vinylpyrrolidone). Examples of the disintegrant include agar powder, sodium hydrogencarbonate, sodium lauryl sulfate, and stearyl monoglyceride. Examples of the lubricant include purified talc, a stearic acid salt, borax, and polyethylene glycol. Examples of the colorant include β-carotene, yellow iron sesquioxide, and caramel. Examples of the sweetening agent include sucrose and bitter orange peel.

In one preparation procedure of an oral liquid formulation, an additive such as a sweetening agent, a buffer, a stabilizer, or a preservative is added to the agents, and the mixture is processed, through a routine method, into oral liquid, syrup, elixir, etc. Such additives may be those generally employed in the art. Examples of sweetening agents include sucrose. Examples of the buffer include sodium citrate. Examples of the stabilizer include traganth. Examples of the preservative include p-oxybenzoic acid ester.

In one preparation procedure of an injection, a pH-regulator, a stabilizer, a tonicity agent, etc. are added to the agents, and the mixture is processed, through a routine method, into subcutaneous, intramuscular, and intravenous injections. Such additives may be those generally employed in the art. Examples of the pH-regulator include sodium phosphate. Examples of the stabilizer include sodium pyrosulfite. Examples of the tonicity agent include sodium chloride.

No particular limitation is imposed on the mode of administration of the drug of the present invention. The two agents may be administered simultaneously, or separately with an interval. In other words, a pitavastatin compound, and amlodipine or a salt thereof may be formulated into a single drug, or may be separately formed into drug products, which may be incorporated in combination into a kit. When the two agents are formed into separate drug products, these drug products do not necessarily have the same drug form. These agents may be administered at different frequencies.

In the present invention, when a single drug containing the two agents is administered, the ratio by mass of the pitavastatin compound to amlodipine or a salt thereof is preferably 1:0.05 to 1:50, more preferably 1:0.1 to 1:10.

In the present invention, the dose of each agent is appropriately selected in accordance with the condition of the patient to which the agent is administered, so long as the dose is an effective amount. Preferably, the daily dose of a pitavastatin compound is 0.01 to 50 mg, more preferably 0.1 to 10 mg, while the daily dose of amlodipine or a salt thereof is preferably 1 to 50 mg, more preferably 2.5 mg to 20 mg. The administration may be once a day or may be divided into twice or more.

EXAMPLES

The present invention will next be described in more detail by way of example, which should not be construed as limiting the invention thereto.

Example 1

Pitavastatin calcium (hereinafter referred to simply as pitavastatin) and amlodipine besylate (hereinafter referred to simply as amlodipine) were administered in combination to a subject, and plasma triglyceride-lowering action and hyperinsulinemia-ameliorating action were evaluated through the following test procedure.

1. Tested Animal and Breeding Conditions

Male Sprague Dawley rats aged 7 weeks (Clea Japan, Inc.) were fed in a breeding room in which a bright dark cycle was maintained (bright duration by a room light: 7 a.m. to 7 p.m.) at a temperature and a humidity of 23±3° C. and 55±15% throughout the test period. The rats were allowed to take a solid chow (CE2; product of Oriental Yeast Co., Ltd.) and 25% aqueous fructose, ad libitum.

2. Drug Preparation

Each of pitavastatin and amlodipine was suspended in 1.0-mass % aqueous solution of hydroxypropylmethyl cellulose (product of Shin-Etsu Chemical Co., Ltd.) in such an amount that the dose thereof was adjusted to 1 mL/kg. The suspension was refrigerated at 4° C. in a shaded bottle. Each drug was prepared every 7 days.

3. Test Method

After the rats had been fed ad libitum with 25% aqueous fructose for two weeks, plasma triglyceride level was measured by means of a Triglyceride E Test Wako (product of Wako Pure Chemical Industries, Ltd.). Among the rats, those having undesirably low plasma triglyceride levels were removed, and the following groups were provided. Specifically, 48 rats were divided into four groups (each including 12 rats) such that the average plasma triglyceride levels were equalized. The four groups were (1) a control group, (2) a pitavastatin alone (10 mg/kg)-administration group, (3) an amlodipine alone (15 mg/kg)-administration group, and (4) a pitavastatin (10 mg/kg) and amlodipine (15 mg/kg)-combined administration group.

Pitavastatin and amlodipine were orally administered once a day (4 p.m.) repeatedly for 21 days. To the control group, a 1.0-mass % aqueous solution of hydroxypropylmethyl cellulose sodium was orally administered at 1 mL/kg once a day (4 p.m.). For each group, blood was collected from each rat 22 hours after final administration, and the plasma triglyceride level was measured by means of a Triglyceride E Test Wako (product of Wako Pure Chemical Industries, Ltd.), and the plasma insulin level was measured by means of a Levis insulin kit (product of Shibayagi Co., Ltd.).

4. Statistical Analysis and Data Processing Method

The determined average levels of each group are represented by average value±standard deviation. The difference between each administration group and the control group was analyzed through Dunnett's parametric test, and P values of 5% or less ($p<0.05$) were considered statistically significant. The synergistic effect was evaluated in accordance with the Burgi formula.

Figure 2:
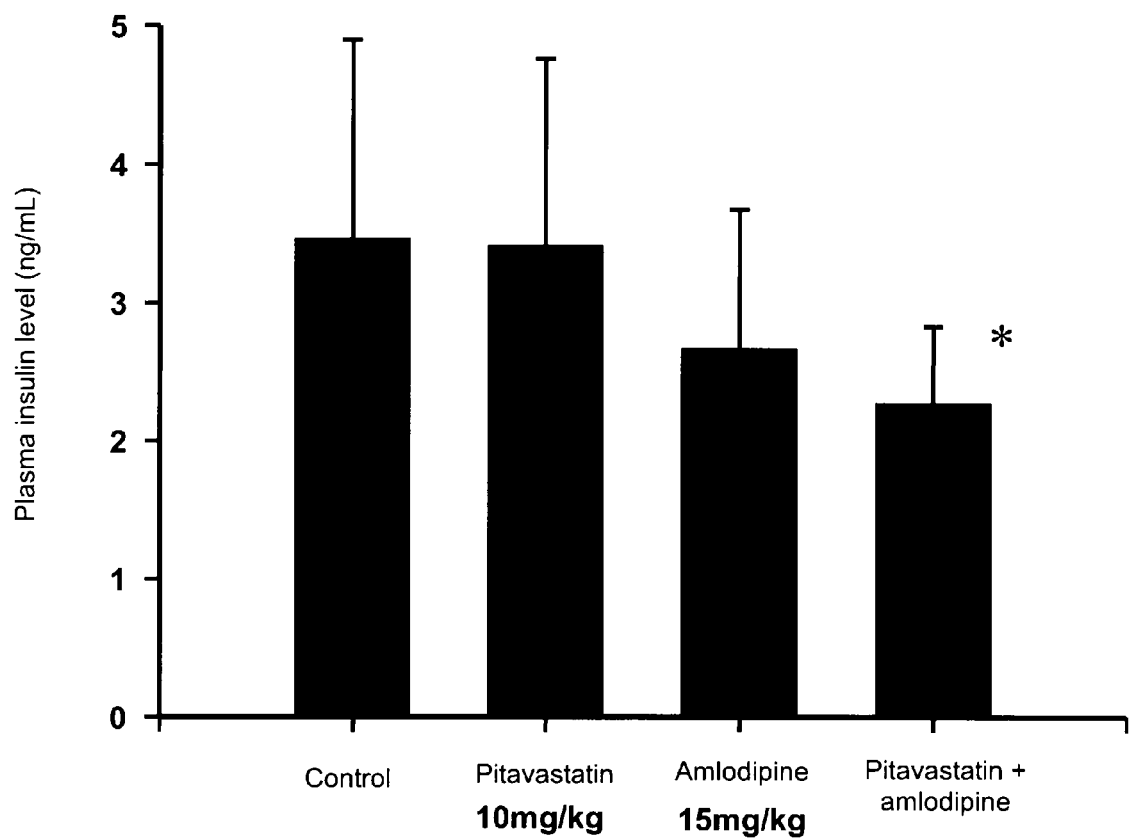
FIG. 2: A graph showing an effect of single or combined administration of pitavastatin calcium (described simply as pitavastatin) and amlodipine besylate (described simply as amlodipine) on plasma insulin level.

FIGS. 1 and 2 show the results. As shown in FIG. 1, plasma triglyceride levels of the pitavastatin alone group and the amlodipine alone group were almost equivalent to those of the control group. In contrast, through administration of the two agents in combination, the plasma triglyceride level was significantly lowered ($p<0.01$). Through calculation with the Burgi formula, the relative plasma triglyceride level of the pitavastatin-amlodipine combination group (0.554, based on the control group) was lower than the product of the relative levels of the agent alone groups (0.966×0.831=0.803), thereby confirming a synergistic lowering effect.

As shown in FIG. 2, plasma insulin levels of the pitavastatin alone group and the amlodipine alone group were not significantly changed as compared with the control group. In contrast, the plasma insulin level was significantly lowered ($p<0.05$) through the combined administration. Through calculation with the Burgi formula, the relative plasma insulin level of the pitavastatin-amlodipine combination group (0.657, based on the control group) was lower than the product of the relative levels of the agent alone groups (0.971× 0.771=0.749), confirming a synergistic lowering effect.

Therefore, combined administration of pitavastatin and amlodipine was found to exhibit a remarkably excellent effect of lowering plasma triglyceride level and plasma insulin level, as compared with the cases where the respective agents were administered alone.

The invention claimed is:

1. A method for lowering triglyceride, comprising administering a therapeutically effective amount of a pitavastatin compound, and amlodipine or a salt thereof to a subject in need thereof.

2. The method for lowering triglyceride as described in claim 1, wherein the pitavastatin compound is pitavastatin calcium.

3. The method for lowering triglyceride as described in claim 1, wherein the salt of amlodipine is amlodipine besylate.

4. A method for treatment of hypertriglyceridemia, comprising administering a therapeutically effective amount of a pitavastatin compound, and amlodipine or a salt thereof to a subject in need thereof.

5. The method as described in claim 4, wherein the pitavastatin compound is pitavastatin calcium.

6. The method as described in claim 4, wherein the salt of amlodipine is amlodipine besylate.

7. The method for lowering triglyceride as described in claim 2, wherein the salt of amlodipine is amlodipine besylate.

8. The method as described in claim 5, wherein the salt of amlodipine is amlodipine besylate.

9. The method as described in claim 1, wherein the ratio by mass of the pitavastatin compound to amlodipine or a salt thereof is 1:0.05 to 1:50.

10. The method as described in claim 1, wherein the ratio by mass of the pitavastatin compound to amlodipine or a salt thereof is 1:0.1 to 1:10.

11. The method as described in claim 4, wherein the ratio by mass of the pitavastatin compound to amlodipine or a salt thereof is 1:0.05 to 1:50.

12. The method as described in claim 4, wherein the ratio by mass of the pitavastatin compound to amlodipine or a salt thereof is 1:0.1 to 1:10.

* * * * *